United States Patent [19]

Abramson et al.

[11] 4,412,956
[45] Nov. 1, 1983

[54] PROCESS FOR FORMING ALKYL VANADATES USING A CATALYST

[75] Inventors: Alan Abramson, White Plains; George C. Ciomo, Hastings-on-Hudson; Gershon J. Davis, White Plains; Edward D. Weil, Hastings-on-Hudson, all of N.Y.

[73] Assignee: Stauffer Chemical Company, Westport, Conn.

[21] Appl. No.: 287,390

[22] Filed: Jul. 27, 1981

[51] Int. Cl.³ .............................................. C07F 9/00
[52] U.S. Cl. ................................................ 260/429 R
[58] Field of Search ................................... 260/429 R

[56] References Cited

U.S. PATENT DOCUMENTS

| | | | |
|---|---|---|---|
| 3,652,617 | 3/1972 | Termin et al. | 260/429 R |
| 3,657,295 | 4/1972 | McCoy | 260/429 R |
| 3,772,355 | 11/1973 | Merz | 260/429 R X |
| 3,987,074 | 10/1976 | Haas et al. | 260/429 R |
| 4,014,911 | 3/1977 | Muntz et al. | 260/429 R |
| 4,014,912 | 3/1977 | Muntz et al. | 260/429 R |

OTHER PUBLICATIONS

Chemical Abstracts 73 67035r (1970).

*Primary Examiner*—Helen M. S. Sneed
*Attorney, Agent, or Firm*—Richard P. Fennelly

[57] ABSTRACT

Alkyl vanadates are formed by the reaction of vanadium pentoxide and an alkyl alcohol in the presence of an azeotroping solvent to assist in the removal of by-product water, using an effective amount of a basic nitrogenous compound as a catalyst.

8 Claims, No Drawings

PROCESS FOR FORMING ALKYL VANADATES USING A CATALYST

BACKGROUND OF THE INVENTION

1. Field of the Invention

The present invention is a process for forming alkyl vanadates.

2. Description of the Prior Art

Alkyl vanadates, which are useful as catalysts, can be formed by the reaction of vanadium pentoxide and an alkyl alcohol. A recent patent which describes this type of reaction is U.S. Pat. No. 3,987,074 to R. Haase. In such processes, by-product water is removed to help drive the reaction to completion, for example, by the incorporation of a suitable azeotroping solvent.

The prior art has suggested the use of certain catalysts in the above-described reaction, U.S. Pat. No. 3,652,617 to E. Termin et al. indicates that strongly acidic substances are useful as catalysts, whereas German Offenlegungschrift No. 1,816,386 also indicates the use of acidic substances as catalysts, including sulfuric and hydrochloric acids, phenyl sulfonic acid, and para-methyl sulfonic acid.

SUMMARY OF THE INVENTION

The present invention is an improved process for the production of alkyl vanadates by the reaction of vanadium pentoxide and an alkyl alcohol in the presence of an azeotroping solvent, wherein a catalytically effective amount of a basic nitrogenous compound is used.

DESCRIPTION OF PREFERRED EMBODIMENTS

The reactants that are used in practicing the present invention and vanadium pentoxide and an alkyl alcohol. The selection of the alkyl alcohol will depend upon the alkyl group desired in the alkyl vanadate product. Use of alkyl alcohols containing any of the $C_2$ and $C_6$ straight or branched alkyl groups is contemplated in accordance with the present invention. Branched chain alcohols are generally preferred, since they yield a vanadate product having improved thermal stability. Representative examples of such alkyl alcohols include ethanol, butanol, isobutanol, amyl alcohol, and isoamyl alcohol. The use of an excess amount of alcohol is preferred since it tends to increase the rate of reaction. Generally, the mole ratio of alkyl alcohol to vanadium pentoxide can vary from about 3:1 to 12:1.

In accordance with the present invention a suitable azeotroping agent is used to assist in the removal of by-product water from the reaction medium and thus held drive the reaction to completion. Examples of suitable aromatic solvents that have been proposed by various prior art investigators include toluene and benzene. It is, however, preferred to use an alkane azeotroping solvent, such as heptane, as described in U.S. application Ser. No. 245,868, filed Mar. 20, 1981, now U.S. Pat. No. 4,351,775 which is incorporated herein by reference.

In selecting the particular azeotroping agent, one should select one which insures that by-product water from the reaction will preferentially co-distill with the solvent at a high concentration of water. The boiling point of the alcohol should also be high enough to ensure that it is present to assist in the removal of the water when the reaction is taking place. Its boiling point should not be so high as to decompose the desired vanadate produce or to require the input of excessive amounts of heat energy to initiate and sustain the desired reaction. It is also preferred, in certain embodiments, that the solvent be less dense than water to produce water as the heavier phase in the separation apparatus to assist in its removal. Generally, the amount of azeotroping solvent to alcohol, for example, can range from about 0.05:1 to about 3:1 on a weight basis.

The present invention is specifically directed to catalysis of the aforementioned type of reaction by use of a catalytically effective amount of a basic nitrogenous compound. The basic nitrogenous compound is one which is capable of providing a basic nucleophilic entity to the reaction medium to catalyze the reaction. Compounds having a structure in which the electron pair on the nitrogen atom is readily available are preferred. Basic nitrogenous compounds having double bonds between the nitrogen atom or atoms and an adjacent carbon atom, or which have a carbonyl group on the adjacent carbon atom, are not preferred since they are less effective as catalysts. Also, the use of relatively insoluble basic nitrogenous compounds is not preferred for the same reason. In general terms, the amount of such catalyst can range from about 0.1% to about 25%, by weight, or more, of the vanadium pentoxide content. The upper limit is principally dictated by economic considerations and also by the possibility that at such higher concentrations, the compound may release excessive amounts of ammonia from the reaction.

Examples of some suitable basic nitrogenous compounds include ammonia; ammonium compounds, such as ammonium hydroxide, ammonium carbonate, ammonium phosphate (dibasic), and ammonium metavanadate; amine compounds, such as triethylamine; the dialkyl formamide compounds, such as dimethyl formamide; urea; pyridine; guanidine carbonate; and the like.

The reaction is conducted by admixing the desired quantities of vanadium pentoxide, alkyl alcohol, solvent, and catalyst in a reaction vessel and refluxing the contents of the reactor while preferably maintaining an inert gas blanket over the reaction mixture during the initial stages of the reaction. During the refluxing operation, the condensed liquid is passed through a trap where a hydrocarbon rich layer will form. Drawing off the water rich layer will remove a portion of the water of formation while the remaining liquid (a mixture of alcohol and solvent) is returned to the reactor. In order to achieve the highest yield in the shortest possible time, use of a packed column having a large diameter to encourage high throughputs of liquid is preferred. If it is desired to recover unused vanadium components (for example, vanadium pentoxide) from the reaction vessel, this can be readily accomplished by filtering the contents of the reactor after the reaction is performed. If desired, the filtrate containing alcohol, solvent and possibly some product can be distilled to remove alcohol and solvent from the product to achieve the highest yield desired.

The present invention is illustrated by the Examples which follow:

EXAMPLE 1

This Example comprises a series of runs which illustrate the improvement obtained by using the present invention.

Run A was a control run in which no catalyst was used.

Run B employed urea as a catalyst.
Run C used ammonium carbonate as a catalyst.
Run D employs both urea and ammonium carbonate as catalysts.

Runs A–C were conducted in a 1 liter flask equipped with a reflux condenser and DEAN-STARK trap, whereas Run D was conducted in a 5 liter flask equipped with reflux condenser, DEAN-STARK trap and packed distillation column. The reagents for the reaction, as described in the following Table, were added to the flask, and the agitator was turned on. Heat was applied so that refluxing began, and the reaction was run until no more water was formed. The resulting mixture was cooled to 25° C., and the unreacted vanadium pentoxide was filtered to yield a filter cake. The filtrate was then recharged to the initial flask, and the n-heptane and isobutanol were distilled under vacuum, applying heat gradually to avoid foaming. The product in the flask was cooled to 25° C. and (for Runs B to D) filtered to retrieve the unused catalyst. The remaining tri(isobutyl)vanadate endproduct was weighed, and the percent yield determined.

TABLE

| | RUN | | | |
|---|---|---|---|---|
| | A | B | C | D |
| Vanadium pentoxide (gm.) | 137.8 | 137.8 | 137.8 | 409.5 |
| Isobutyl alcohol (gm.) | 507.6 | 507.6 | 507.6 | 1498.0 |
| n-heptane solvent (gm.) | 84.6 | 84.6 | 84.6 | 675.0 |
| Urea catalyst (gm.) | — | 6.9 | — | 22.5 |
| Ammonium carbonate catalyst (gm.) | — | — | 6.9 | 20.0 |
| Reflux temp. (°C.) | 96.5 | 95.5 | 95.0 | 91.0 |
| Reaction time (hrs.) | 7.5 | 11.5 | 15.0 | 10.5 |
| End temp. (°C.) | 103.5 | 110 | 108.0 | 101.0 |
| $H_2O$ collected (cc.) | 21.1 | 32.6 | 42.0 | 127.9 |
| Filtration time (min.) | 90 | 33 | 120 | 10 |
| Filter diameter (cm.) | 7 | 7 | 7 | 15 |
| Filter cake Wt. (gm.) | 103.9 | 59.1 | 24.3 | 70.6 |
| Distill. temp. (°C.) | 97 | 94 | 90 | 99 |
| Vacuum pressure (mm. Hg.) | 14 | 13 | 15 | 18 |
| Catalyst recovered (gm.) | — | 11.7 | — | 16 |
| Product obtained (gm.) | 217 | 307 | 371 | 1159 |
| % Yield of product | 50.0 | 70.8 | 85.6 | 90.0 |

In Run A, in which no catalyst was employed, the yield was 50% under the conditions employed. Use of urea in Run B gave two advantages: A higher yield (70.8%) and faster filtration rate for the unreacted vanadium pentoxide. The ammonium carbonate catalyst in Run C gave a very high yield (85.6%) but produced a slower filtration rate for the unreacted vanadium pentoxide. In Run D, a combined urea/ammonium carbonate catalyst and use of a distillation column gave the highest yield (90.0%) and the fastest filtration time for the unreacted vanadium pentoxide.

EXAMPLE 2

This Example illustrates the results obtained by using ammonium hydroxide as a catalyst. The procedure described in Example 1 was employed. The Table sets forth the data:

TABLE

| Vanadium pentoxide (gm.) | 137.8 |
|---|---|
| Isobutyl alcohol (gm.) | 507.6 |
| n-heptane solvent (gm.) | 84.6 |
| Ammonium hydroxide catalyst (gm.) | 2.6 |
| Reflux temp. (°C.) | 95 |
| Reaction time (hrs.) | 11.5 |
| End temp. (°C.) | 104.5 |
| $H_2O$ collected (cc.) | 31.1 |
| Filtration time (min.) | 106 |
| Filter diameter (cm.) | 7 |
| Filter cake Wt. (gm.) | 65.7 |
| Distill. temp. (°C.) | 89–97° |
| Vacuum press. (mm. Hg.) | 14 |
| Catalyst recovered (gm.) | None |
| Product obtained (gm.) | 293.5 |
| % Yield of product | 67.8 |

The ammonium hydroxide was found to be approximately as effective a catalyst, under the conditions employed, as the urea catalyst used in Example 1, Run B, but a less effective one than the ammonium carbonate catalyst used in Example 1, Run C. The product formed by this reaction was of a blackish color. The filtration time in this Example was longer than for Run B of Example 1, but shorter than for Run C of Example 1.

EXAMPLE 3

In this Example, dimethyl formamide, pyridine, and ammonium carbonate were tested as catalysts using the procedure described in Example 1.

Run A employed dimethyl formamide, Run B, pyridine, and Run C, ammonium carbonate. The Table sets forth the data:

TABLE

| | RUN | | |
|---|---|---|---|
| | A | B | C |
| Vanadium pentoxide (gm.) | 137.8 | 137.8 | 137.8 |
| Isobutyl alcohol (gm.) | 507.6 | 507.6 | 507.6 |
| n-heptane solvent (gm.) | 84.6 | 84.6 | 84.6 |
| Dimethyl formamide catalyst (gm.) | 6.9 | — | — |
| Pyridine catalyst (gm.) | — | 6.9 | — |
| Ammonium carbonate catalyst (gm.) | — | — | 6.9 |
| Reflux temp. (°C.) | 96.5 | 95.5 | 93.5 |
| Reaction time (hrs.) | 6 | 6 | 9.1 |
| End temp. (°C.) | 102.5 | 102.5 | 107 |
| $H_2O$ collected (cc.) | >22.2 | 21.6 | 38.3 |
| Filtration time (min.) | — | — | 71 |
| Filter diameter (cm.) | — | — | 7 |
| Filter cake wt. (gm.) | — | — | 40.8 |

Dimethyl formamide and pyridine were less effective as catalysts than ammonium carbonate under the test conditions that were employed although they gave an improvement over the use of no catalyst (e.g., Example 1, Run A).

EXAMPLE 4

This Example shows a run using an ammonium carbonate catalyst utilizing the procedure shown in Example 1. The following data was obtained:

TABLE

| Vanadium pentoxide (gm.) | 137.8 |
|---|---|
| Isobutyl alcohol (gm.) | 507.6 |
| n-heptane solvent (gm.) | 84.6 |
| Ammonium carbonate catalyst (gm.) | 6.9 |
| Reflux temp. (°C.) | 95 |
| Reaction time (hrs.) | 15 |
| End temp. (°C.) | 108 |
| $H_2O$ collected (cc.) | 42.0 |
| Filtration time (min.) | 120 |
| Filter diameter (cm.) | 7 |
| Filter cake wt. (gm.) | 24.3 |
| Distill. temp. (°C.) | 90° |
| Vacuum press. (mm. Hg.) | 15 |
| Catalyst recovered (gm.) | None |
| Product obtained (gm.) | 371.0 |

| TABLE-continued | |
|---|---|
| % Yield of product | 85.6 |

EXAMPLE 5

This Example shows the use of ammonium metavanadate (Run A) and ammonium phosphate, dibasic (Run B) as catalysts. The following data was obtained:

TABLE

| | RUN | |
|---|---|---|
| | A | B |
| Vanadium pentoxide (gm.) | 137.8 | 137.8 |
| Isobutyl alcohol (gm.) | 507.6 | 507.6 |
| n-heptane solvent (gm.) | 84.6 | 84.6 |
| Ammonium metavanadate catalyst (gm.) | 6.9 | — |
| Ammonium phosphate, dibasic catalyst (gm.) | — | 6.9 |
| Reflux temp. (°C.) | 95 | 95 |
| Reaction time (hrs.) | 11.5 | 3.9 |
| End temp. (°C.) | 105 | 102 |
| $H_2O$ collected (cc.) | 35.1 | 19.3 |
| Filtration time (min.) | >150 | — |

The amount of water collected in Run A amounted to 78% of theoretical. Run B was turned off at a relatively early point when the reaction began to slow down. If completed, it was estimated that the yield would be about 5–10% above the yield obtained using no catalyst.

EXAMPLE 6

This Example illustrates the catalytic effect for ammonium metavanadate (Run A) and ammonium carbonate (Run B) and illustrates (in Run C), for comparative reasons, that an acidic nitrogen catalyst, ammonium phosphate, monobasic [$(NH_4)H_2PO_4$], does not function as a catalyst. The procedure of Example 1 was used.

TABLE

| | RUN | | |
|---|---|---|---|
| | A | B | C |
| Vanadium pentoxide (gm.) | 137.8 | 137.8 | 137.8 |
| Isobutyl alcohol (gm.) | 507.6 | 507.6 | 507.6 |
| n-heptane solvent (gm.) | 84.6 | 84.6 | 84.6 |
| Ammonium metavanadate catalyst (gm.) | 17.23 | — | — |
| Ammonium carbonate catalyst (gm.) | — | 2.76 | — |
| Ammonium phosphate, monobasic (gm.) | — | — | 6.89 |
| Reflux temp. (°C.) | 95 | 94.5 | 96 |
| Reaction time (hrs.) | 8.2 | 8 | 3[1] |
| End temp. (°C.) | 106 | 105 | 101 |
| $H_2O$ collected (cc.) | 35.5 | 34.6 | 12.9 |
| Filtration time (min.) | 46* | ** | — |
| Filter diameter (cm.) | 7 | ** | — |
| Filter cake wt. (gm.) | 91* | ** | — |

[1] the reaction in Run C was terminated after only three hours because of a decrease in the rate of water that was observed leaving the reaction. This was indicative of a slowing of the reaction at this point.
*an unknown amount of a filter aid (SOLKA-FLOC) was used. The filter cake weight is higher due to use of this filter aid.
**additional (2.76 gm.) of ammonium carbonate was added, and the reaction was continued 259 min. longer (102.5° to 107.5° C.). The total water collected was 40.3 cc. After the reaction was completed, the solvent was stripped without prior filtration. The remaining liquid was then filtered warm. Filtration time was 95 min. Product weight was 358.1 gm. representing a yield of 82.7%. The total filter cake was 28.6 gm. In Run C, the reaction was terminated without a filtration step when it became apparent that the amount of water collected was lower than the amount in a control run (e.g., see Example 1, Run A).

EXAMPLES 7-14

The procedure used in Example 1 was employed to test the effectiveness of a series of compounds as catalysts in accordance with the present invention. The Tables set forth below illustrate the results obtained.

| Example | Tested Compound | Weight |
|---|---|---|
| 7 (Control) | None | — |
| 8 (Control) | None | — |
| 9 (Control) | None | — |
| 10 | Urea | 3.2 gm. |
| 11 | Dicyandiamide | 3.2 gm. |
| 12 | Melamine | 3.3 gm. |
| 13 | Guanidine carbonate | 3.1 gm. |
| 14 | Triethylamine | 3.2 gm. |

| Example | Heptane (gm.) | Isobutanol (gm.) | $V_2O_5$ (gm.) | Time at Reflux (hrs.) |
|---|---|---|---|---|
| 7 (Control) | 650 | 444 | 182 | 9.75 |
| 8 (Control) | 650 | 444 | 182 | 8.5 |
| 9 (Control) | 108 | 444 | 182 | 8.5 |
| 10 | 325 | 222 | 91 | 9 |
| 11 | 325 | 222 | 91 | 6 |
| 12 | 325 | 222 | 91 | 2 |
| 13 | 325 | 222 | 91 | 4 |
| 14 | 325 | 222 | 91 | 4.5 |

| Example | Temp. (°C.) (Start–End) | $H_2O$ Off (wt.) | Approx. Yield TIBV (%) |
|---|---|---|---|
| 7 (Control) | 77–94 | 23.5 cc. | 39.1 |
| 8 (Control) | 88–98 | * | * |
| 9 (Control) | 94.5–102 | 20.7 gm. | 35.9 |
| 10 | 88.5–97.5 | 17.8 gm. | 61.9 |
| 11 | 89–94 | 10.25 cc. | 34.1** |
| 12 | 89–92 | 5 cc. | 16.6** |
| 13 | 87–94 | 12.5 cc. | 41.6 |
| 14 | 88.5–93 | 13.25 cc. | 44.1 |

*the water byproduct was lost through the condenser. The calculated yield based on triisobutyl vanadate (TIBV) was 39.1%.
**Dicyandiamide (Example 11) and melamine (Example 12) are not preferred catalysts for use in the present invention although both showed some effectiveness. Dicyandiamide exhibited a small effectiveness during the first three hours of the reaction and was only marginally better (about 1–2%) than the control for the next three hours, at which time the reaction was terminated. Melamine is a somewhat insoluble compound in water having double bonds between the nitrogen atom and an adjacent carbon atom. Melamine was an effective catalyst, in accordance with the present invention, during the first half hour of the reaction, but began to become less effective, and it produced a lower yield than the control between the first and second hours, at the end of which time the reaction was terminated.

EXAMPLES 15-41

These Examples illustrate the present invention using the procedure described in Examples 7-14. In these runs, various reaction conditions and reagent combinations were changed.

| Example | Tested Catalyst Compound | Weight (gm.) |
|---|---|---|
| 15 | Urea | 3.2 |
| 16 | Urea | 1.6 |
| 17 | Urea | 3.2 |
| 18 | Urea | 0.5 |
| 19 | Urea | 3.2 |
| 20 | Urea | 3.2 |
| | p-Benzoquinone | 1.0 |
| 21 | Urea | 3.2 |
| 22 | Urea | 3.2 |
| 23 | Urea | 3.2 |
| 24 | Urea | 3.2 |
| 25 (Control) | None | — |

-continued

| Example | Tested Catalyst Compound | Weight (gm.) |
|---|---|---|
| 26 | Urea | 3.2 |
| 27 (Control) | None | — |
| 28 | Urea | 4.8 |
| 29 | Triethylamine | 6.4 |
| 30 | Urea | 9.24 |
| 31 | Urea | 7.66 |
| 32 | Urea | 6.08 |
| 33 | Urea | 6.06 |
| 34 | Urea | 6.89 |
| 35 | Urea | 6.89 |
| 36 (Control) | None | — |
| 37 | Ammonium hydroxide | 2.6 |
| 38 | Urea | 6.89 |
| 39 | Dimethyl formamide | 6.89 |
| 40 | Pyridine | 6.89 |
| 41 | Ammonium carbonate | 6.89 |

| Example | Heptane (gm.) | Isobutanol (gm.) | $V_2O_5$ (gm.) | Time at Reflux (hrs.) |
|---|---|---|---|---|
| 15 | 162.5 | 277.5 | 91 | 2 |
| 16 | 162.5 | 277.5 | 91 | 2 |
| 17 | 325 | 222 | 91 | 7 |
| 18 | 325 | 222 | 91 | 7 |
| 19 | 162.5 | 222 | 91 | 4 |
| 20 | 162.5 | 222 | 91 | 2.5 |
| 21 | 325 | 222 | 101[1] | 5.25 |
| 22 | 325 | 222 | 90.5[2] | 8.5 |
| 23 | 325 | 222 | 95.4[3] | 2 |
| 24 | 395 | 111 | 45.5 | 2 |
| 25 (Control) | 325 | 222 | 109.6[4] | 7 |
| 26 | 135.5 | 444 | 91[5] | 10 |
| 27[6] | 325 | 222 | 91 | 4.5 |
| 28 | 232 | 333 | 91[7] | 9 |
| 29 | 325 | 222 | 91 | 9 |
| 30[8] | None | 607.5 | 91 | 5.3 |
| 31 | 77 | 516 | 91 | 6 |
| 32 | 154 | 424.5 | 91 | 6 |
| 33 | 137 | 444 | 121.2 | 7.5 |
| 34[9] | None | 507.6 | 137.8 | 7.5 |
| 35 | 84.6 | 507.6 | 137.8 | 7.5 |
| 36 (Control) | 84.6 | 507.6 | 137.8 | 7.5 |
| 37 | 84.6 | 507.6 | 137.8 | 11.5 |
| 38 | 84.6 | 507.6 | 137.8 | 11.5 |
| 39 | 84.6 | 507.6 | 137.8 | 6 |
| 40 | 84.6 | 507.6 | 137.8 | 6 |
| 41 | 84.6 | 507.6 | 137.8 | 9 |

[1]includes 10 gm. of filter cake from Example 17.
[2]includes 45 gm. added in increments during reaction.
[3]includes 95.4 gm. wet cake (equivalent to about 73 gm. dry) of recovered $V_2O_5$ from Examples 17, 18, 19, and 22.
[4]includes 18.6 gm. wet $V_2O_5$ recovered from another run.
[5]added in small increments during the reaction.
[6]slow agitation (90–100 rpm) used with blade raised about 0.64 cm.
[7]addition of last 26 gm. made incrementally.
[8]no heptane was added initially and no water was extracted. Hexane (40 gm.) was added 50 min. into the run.
[9]Hexane (84.6 gm.) was used.

| Example | Temp. (°C.) (Start–End) | H₂O Off (cc.) | Approx. Yield TIBV (%) | Filtration Time (min.) |
|---|---|---|---|---|
| 15 | 90–95 | 10.1 | 33.6 | — |
| 16 | 90–95 | 10.4 | 34.6 | — |
| 17 | 87–94.5 | 15.6 | 51.9[10] | 5 |
| 18 | 87–94 | 15.5 | 51.6[10] | 11 |
| 19 | 88.5–95.5 | 11.2 | 37.3 | 6 |
| 20 | 88.5–95 | 9.9 | 32.9 | — |
| 21 | 87–94 | 14.0 | 46.6 | — |
| 22 | 88–95 | 17.75 | 59.4 | 5.25 |
| 23 | 89.5–92.5 | 6.7 | 28 | — |
| 24 | 87–93.5 | 7.0 | 46.6 | — |
| 25 (Control) | 88–93 | 11.15 | 37 | — |
| 26 | 95–100 | 18.1 | 60.2 | — |
| 27 (Control) | 88.5–93.5 | 10.1 | 33.3 | — |
| 28 | 90.97.5 | 20.15 | 67.0 | 5.25 |
| 29 | 88.5–95.5 | 18.3 | 60.9[11] | 15.5 |
| 30 | 96.5–102 | 16.0 | 53.2[12] | — |
| 31 | 96.5–103 | 18.9 | 62.9[12] | — |
| 32 | 92.5–99 | 18.8 | 62.6[12] | — |
| 33 | 92.5–100.5 | 23.15 | 57.8[13] | 14.75 |
| 34 | 85–92 | 24.35 | 53.5[13] | 18.5 |
| 35 | 95.5–105 | 30.3 | 66.6[13] | 25.5 |
| 36 | 96.5–103.5 | 21.05 | 46.3 | 90 |
| 37 | 95–104.5 | 31.1 | 68.3[14] | 106 |
| 38 | 95.5–104.5[15] | 32.65 | 71.7[14] | 33 |
| 39 | 96.5–102.5 | 23 | 50.5 | — |
| 40 | 95.5–102.5 | 21.6 | 47.5 | — |
| 41 | 93.5–107 | 38.3 | 84.2 | 71 |

[10]The product from Example 17 was of somewhat redder appearance than the product from Example 18.
[11]The product from this Example was green and was greener than the product from any other run.
[12]For Examples 30–32, the product was Example 30 was most green in color; from Example 32, was most red.
[13]For Examples 33–35, the product from Example 34 was more red than the product from Example 33. The product from Example 35 was the most green.
[14]The product from Example 38 was more red than the product from Example 37.
[15]The temperature reached 110° C. for the last half hour.

EXAMPLES 42–65

These Examples illustrate additional testing of compounds as catalysts under a variety of reaction conditions in accordance with the present invention.

| Example | Tested Catalyst Compound | Weight (gm.) |
|---|---|---|
| 42 | Ammonium carbonate | 6.89 |
| 43 | Ammonium vanadate | 6.89 |
| 44 | Diammonium phosphate | 6.89 |
| 45* | Monoammonium phosphate | 6.89 |
| 46 | Ammonium vanadate | 17.23 |
| 47 | Ammonium carbonate | 2.76 |
| 48* | Potassium carbonate | 6.89 |
| 49 | Ammonium carbonate | 6.89 |
| 50 | Ammonium carbonate | 13.78 |
| 51 | Ammonium carbonate | 34.45 |
| 52 | Ammonium carbonate | 31.0 |
| 53 | Ammonium carbonate | 6.89 |
| 54 | Ammonium carbonate | 27.56 |
| 55 | Ammonium carbonate | 6.89 |
| 56 | Ammonium carbonate | 31.0 |
| 57 | Ammonium carbonate | 6.89 |
| 58 | Ammonium carbonate<br>Urea | 4.5<br>5.0 |
| 59 | Ammonium carbonate | 4.5 |
| 60 | Ammonium carbonate | 6.89 |
| 61 | Ammonium carbonate<br>Urea | 4.5<br>1.0 |
| 62 | Ammonium carbonate<br>Urea | 4.5<br>3.0 |
| 63 | Ammonium carbonate<br>Urea | 4.5<br>5.0 |
| 64 | Ammonium carbonate<br>Urea | 4.5<br>5.0 |
| 65 | Ammonium carbonate<br>Urea | 20.0<br>22.5 |

*comparative run. Not part of the present invention. Monoammonium phosphate is acidic (Ex. 6).

| Example | Heptane (gm.) | Isobutanol (gm.) | $V_2O_5$ (gm.) | Time at Reflux (hrs.) |
|---|---|---|---|---|
| 42 | 84.6 | 507.6 | 137.8 | 15 |
| 43 | 84.6 | 507.6 | 137.8 | 11.5 |
| 44 | 84.6 | 507.6 | 137.8 | 4 |
| 45 | 84.6 | 507.6 | 137.8 | 3 |

-continued

| Example | Heptane (gm.) | Isobutanol (gm.) | $V_2O_5$ (gm.) | Time at Reflux (hrs.) |
|---|---|---|---|---|
| 46 | 84.6 | 507.6 | 137.8 | 8 |
| 47 | 84.6 | 507.6 | 137.8 | 8 |
| 48 | 84.6 | 507.6 | 137.8 | 4 |
| 49 | 84.6 | 507.6 | 137.8 | 9.5 |
| 50 | 84.6 | 507.6 | 137.8 | 9.5 |
| 51 | 423 | 2538 | 689 | 15.5 |
| 52 | 380.7 | 2284 | 620 | 7 |
| 53 | 84.6 | 507.6 | 137.8 | 8.5 |
| 54 | 676.8 | 2030.4 | 551.2 | 15 |
| 55 | 232 | 333 | 91 | 6.5 |
| 56 | 380.7 | 2284 | 620.1 | 11 |
| 57 | 232 | 333 | 91 | 4.5 |
| 58 | 232 | 333 | 91 | 6.5 |
| 59 | 232 | 333 | 91 | 6.0 |
| 60 | None | 333 | 91 | 9.5 |
| 61 | 232 | 333 | 91 | 5.5 |
| 62 | 232 | 333 | 91 | 5.5 |
| 63 | 116 | 333 | 91 | 5.75 |
| 64 | 150 | 333 | 91 | 5.5 |
| 65 | 675 | 1498 | 409.5 | 10.5 |

| Example | Temp. (°C.) (Start–End) | $H_2O$ Off (cc.) | Approx. Yield TIBV (%) | Filtration Time (min.) |
|---|---|---|---|---|
| 42 | 95–108 | 42 | 93.3 | 120[1] |
| 43 | 95–105 | 35.1 | 78.0 | >150 |
| 44 | 95–102 | 19.3 | —[2] | — |
| 45 | 96–101 | 12.9 | —[2] | — |
| 46 | 95–106 | 35.5 | 78.9 | 46[1] |
| 47 | 94.5–105[3] | 34.6 | 76.9[3] | —[3] |
| 48 | 95–101.5 | 17.9 | — | — |
| 49 | 95–105 | 33.1 | 73.6 | 125[4] |
| 50 | 94–106 | 36.5 | 81.1 | 32 |
| 51 | 90–101 | 133.6 | —[5] | —[5] |
| 52 | 92–95.5 | 6 | —[5] | —[5] |
| 53 | 96–108.5 | 43.4 | 96.4[6] | — |
| 54 | 93–102.5 | 170.7 | 93.8 | —[7] |
| 55 | 91–98 | 29.2 | 98.3 | >270 |
| 56 | 97–107 | 185 | 91.4 | Poor[8] |
| 57 | 91–96.5 | 22.8 | 76.8 | — |
| 58 | 91–98 | 27.1 | 91.2 | 10 |
| 59 | 91–98[9] | 28.5 | 96.0 | 41 |
| 60 | 82.88.5 | 29.8 | 100[10] | — |
| 61 | 90–99.5 | 24.9 | 83.8 | 25 |
| 62 | 90–98 | 26.0 | 87.5 | 11 |
| 63 | 93.5–104.5 | 29.0 | 97.6 | 12 |
| 64 | 91–101 | 26.5 | 89.2 | 12 |
| 65 | 91–101 | 127.9 | 95.7 | 10 |

[1] used SOLKA-FLOC filter aid during the filtration step.
[2] slow reaction.
[3] added 2.76 gm. of additional catalyst after 8 hours. Continued refluxing for an additional 4.5 hours allowing the temperature to rise to 107.5° C. A total of 40.3 cc. of $H_2O$ came off indicating an 89.6% yield. The solvent was removed. The filtration time was 100 min.
[4] used 1 gm. NUCHAR SN brand and 3 gm. SOLKA-FLOC filter aid.
[5] run discarded because of slower than anticipated reaction rates.
[6] used a Vigreaux distillation column.
[7] five different filtrations were conducted in an attempt to improve filtration time.
[8] flocculating agents added.
[9] 5 gm. of urea was added at the end of the reaction to attempt to improve filtration.
[10] a slimy suspension resulted which was discarded.

EXAMPLES 66–72

The following Table illustrates a further series of reactions using the present invention. Example 66 utilized a Vigreaux column (30.48 cm. length; 2.54 cm. diameter). All other runs used a vacuum jacketed, Goodloe packed column (30.48 cm. length; 2.54 cm. diameter). The catalyst in Example 66 was 5 gm. ammonium carbonate and 4.5 gm. urea. In all other runs it was 20.25 gm. ammonium carbonate and 22.5 gm. urea. Examples 67–72 were on a five liter scale.

| Example | Solvent | Wt. (gm.) | Isobutanol (gm.) | $V_2O_5$ (gm.) |
|---|---|---|---|---|
| 66 | Toluene | 150 | 333 | 91 |
| 67 | Cyclohexane | 675 | 1498.5 | 409.5 |
| 68 | Toluene | 675 | 1498.5 | 409.5 |
| 69 | Heptane | 740 | | |
|   | Hexane | 35 | 1498.5 | 409.5 |
| 70 | Heptane | 675 | 1498.5 | 409.5 |
| 71 | Heptane | 675 | 1498.5 | 409.5 |
| 72 | Heptane | 1915.6 | 1498.5 | 409.5 |

| Example | Time at Reflux (hrs.) | Temp. (°C.) (Start–End) | $H_2O$ Off (cc.) |
|---|---|---|---|
| 66 | 4½ | 98–110 | 26.7 |
| 67 | 1.75 | 80–86 | 29.1 |
| 68 | 2 | 97.5–103 | 54.8 |
| 69 | 2 | 88–93.5 | 38.5 |
| 70 | 14.5 | 89–98.5 | 119.9 |
| 71 | 10 | 89–95 | 80.0 |
| 72 | 12¼ | 93–104 | 128.3 |

| Example | VARIAC[1] Setting | Column Through-Put (cc/min.)[2] | Approx. Yield (%) |
|---|---|---|---|
| 66 | 94 | — | 89.0 |
| 67 | 80 | 30 | 21.6[4] |
| 68 | 85 | — | 40.6[4] |
| 69 | 80 | — | 28.7[4] |
| 70 | 82.5 | 30 | 88.8 |
| 71 | 62.5 | 11 | 59.2[5] |
| 72[3] | 82.5 | 30 | 95.0 |

[1] numbers indicate relative settings on VARIAC apparatus which feeds electrical power to heating mantle.
[2] the rate at which solvents pass through the column measured as the rate at which liquids return to the column from the DEAN-STARK trap. A higher throughput generally results in a higher reaction rate.
[3] very solw filtration time - estimated as 2-4 hours.
[4] the lower yield, compared to Example 66, is due to termination of the reaction after a shorter period of time at reflux.
[5] the lower yield, compared to Example 66, is due to the lower column throughput.

EXAMPLE 73

This example illustrates a particularly preferred embodiment of the present invention utilizing a 378.53 liter reactor equipped with a glass-lined distillation column having a 15.24 cm. inner diameter and a height of 1.83 meters, which had been packed with a high performance stainless steel mesh.

The reactor was first charged with the following:

| INGREDIENT | AMOUNT |
|---|---|
| Isobutanol | 99.79 kg. |
| n-heptane | 45.36 kg. |
| Vanadium pentoxide | 27.22 kg. |
| Urea catalyst | 1.36 kg. |
| Ammonium carbonate catalyst | 1.59 kg. |

The resulting mixture was heated to reflux so that the heptane entrained the water of reaction as it forms. Vapor comprising isobutanol, heptane and water was condensed, and the water was further phase separated in a trap. The isobutanol and heptane were returned to the reaction vessel.

The reaction was allowed to continue for 32 hours until the rate of water removal fell to about 0.045 to 0.068 kg. per hour.

The temperatures (in °C.) that were recorded during the reaction were as follows:

| Temperature | Start of Reflux | During Reaction | End of Reaction |
| --- | --- | --- | --- |
| Reactor | 92 | 102 | 104 |
| Vapor | 88 | 90 | 88 |
| Jacket | 125 | 140 | 140 |

The reactor's contents were allowed to cool to 75° C., and they were then filtered over a period of about 2 hours through a pressure filter. The unreacted vanadium pentoxide was washed with 4.54–6.8 kg. of heptane.

The filtrate was returned to the reactor, and the solvents were stripped at atmospheric pressure first, then at pressures down to 20 mm. Hg. vacuum. The resulting product was cooled to about 20°–25° C. so that all remaining catalyst crystallized. After filtration about 72.57 kg. of a clear, yellow triisobutyl vanadate liquid was obtained at a yield of about 84%. Approximately 1.81 kg. of wet cake remained in the filter.

The foregoing examples are merely illustrative of certain preferred embodiments of the present invention.

The scope of protection is set forth in the claims which follow.

What is claimed:

1. In a process for the formation of alkyl vanadates by the reaction of an alkyl alcohol and vanadium pentoxide in an azeotroping solvent, wherein the improvement comprises the use of a catalytically effective amount of a basic nitrogenous catalyst to increase the yield of product.

2. A process as claimed in claim 1 wherein the amount of catalyst is from about 0.1% to about 25%, by weight of the amount of vanadium pentoxide.

3. A process as claimed in claim 1 wherein the catalyst is one which provides ammonia to the reaction medium.

4. A process as claimed in claim 1 wherein the catalyst is selected from the group consisting of ammonia; ammonium hydroxide, carbonate, phosphate (dibasic), metavanadate; triethylamine, dimethyl formamide, urea, pyridine, and guanidine carbonate.

5. A process as claimed in either claim 1 or 2 wherein the catalyst is selected from the group consisting of urea, ammonium carbonate, and mixtures thereof.

6. A process as claimed in any of claims 1–4 wherein an alkane azeotroping solvent is present.

7. A process as claimed in any of claims 1–4 wherein heptane is used as the azeotroping solvent.

8. A process as claimed in any of claims 1–4 wherein heptane is used as the azeotroping solvent and the catalyst is selected from the group consisting of urea, ammonium carbonate, and mixtures thereof.

* * * * *